United States Patent [19]

Kramer et al.

[11] Patent Number: 4,969,870
[45] Date of Patent: Nov. 13, 1990

[54] METHOD AND APPARATUS FOR INTRAOSSEOUS INFUSIONS

[75] Inventors: George C. Kramer, Davis; William Blaisdell, Sacramento; Jerald M. Henderson; Brian Bay, both of Davis, all of Calif.

[73] Assignee: The Regents of the University of California, Berkeley, Calif.

[21] Appl. No.: 362,858

[22] Filed: Jun. 7, 1989

[51] Int. Cl.⁵ .............................................. A61M 25/00
[52] U.S. Cl. ...................................... 604/51; 604/93; 604/264
[58] Field of Search ................... 604/51, 93, 175, 264, 604/272, 273, 274

[56] References Cited

U.S. PATENT DOCUMENTS

| | | |
|---|---|---|
| 1,272,104 | 7/1918 | Riethmueller . |
| 1,523,068 | 1/1925 | Hein . |
| 2,426,535 | 8/1947 | Turkel . |
| 2,705,949 | 4/1955 | Silverman . |
| 2,773,500 | 12/1956 | Young . |
| 2,773,501 | 12/1956 | Young . |
| 3,310,051 | 3/1967 | Schulte ............................ 604/175 |
| 3,469,574 | 9/1969 | Durkan . |
| 3,750,667 | 8/1973 | Pshenichny et al. . |
| 3,783,876 | 1/1974 | Dye . |
| 4,378,810 | 4/1983 | Ishizaki et al. . |
| 4,496,342 | 1/1985 | Banko . |
| 4,534,756 | 8/1985 | Nelson . |
| 4,710,171 | 12/1987 | Rosenberg . |
| 4,747,414 | 5/1988 | Brossel . |
| 4,763,667 | 8/1988 | Manzo . |
| 4,772,261 | 9/1988 | Van Hoff et al. ................... 604/51 |

OTHER PUBLICATIONS

Rogers, Stephen N., M.D., Jonathan L. Benumof, M.D., "Intraosseous Infusions", 1985, pp. 339-343.
Rosetti, Valerie A., M.D., et al., "Intraosseous Infusion: An Alternative Route of Pediatric Intravascular Access", *Annals of Emergency Medicine*, Sep. 1985, pp. 885-888.
Turkel, Henry, M.D., and Frank H. Bethell, M.D., "A New and Simple Instrument for Administration of Fluids Through Bone Marrow", *War Medicine*, 1944, pp. 222-225.
Tocantins, Leandro M., M.D., et al., "Infusions of Blood and Other fluids Via the Bone Marrow in Traumatic Shock and Other Forms of Peripheral Circulatory Failure", *Annals of Surgery*, Dec. 1941, pp. 1085-1092.
Shoor, Perry M., M.D. et al., "Intraosseous Infusion: Pressure Flow Relationship and Pharmacokinetics", *The Journal of Trauma*, Oct. 1979, pp. 772-774.
Spivey, William H., M.D., et al., "Comparison of Intraosseous, Central, and Peripheral Routes of Sodium Bicarbonate Administration During CPR in Pigs", *Annals of Emergency medicine*, Dec. 1985, pp. 1135-1140.
Hodge, Dee, III, M.D. et al., "*Intraosseous Infusion Flow Rates in Hypovolemic Pediatric Dogs*", Annals of emergency Medicine, Mar. 1987, pp. 305-307.
Berg, Robert a., M.D., "*Emergency Infusion of Catecholamines Into Bone Marrow*", Emergency Infusion, Sep. 1984, pp. 810-811.

*Primary Examiner*—John D. Yasko
*Attorney, Agent, or Firm*—Pretty, Schroeder, Brueggemann, & Clark

[57] ABSTRACT

Apparatus and related method for infusing liquids and drugs into, or aspirating marrow from, the trabecula of a patient's bone. The apparatus enables the user to reliably determine when an enlarged, threaded tip of an infusion/aspiration tube has reached the trabecular bone, and a spring bias ensures that the tip seals the hole formed in cortical bone during the subsequent infusion or aspiration.

20 Claims, 2 Drawing Sheets

METHOD AND APPARATUS FOR INTRAOSSEOUS INFUSIONS

BACKGROUND OF THE INVENTION

This invention relates generally to methods and apparatus for infusing liquids into bone trabecula and/or aspirating bone marrow and, more particularly, to such methods and apparatus in which the depth of entry into the bone is carefully controlled.

Drugs and other liquids are customarily delivered to patients via their vascular systems, using a needle or catheter inserted into a peripheral blood vessel. Such techniques function generally satisfactorily in cases where the patient's blood pressure is at normal levels. However, in cases where the patient is in circulatory shock due to heart failure, drug overdose, or severe hemorrhaging, the peripheral blood vessels frequently are collapsed and access to those blood vessels can be difficult. Peripheral vessel catherization also is exceedingly difficult in pediatric patients because of the small size of their peripheral vessels. Substantial delays in administrating the drugs and liquids can therefore result and, in many instances, vascular access cannot be attained at all. Severe injury to the patient, even death, can therefore result.

In such cases of serious circulatory shock and hemorrhaging, one suitable alternative to vascular infusion is intraosseous infusion. In particular, the resuscitative fluid or drug solution is injected directly into the relatively porous trabecula of the patient's bone. Typically, the sternum, femur, tibia, or other long bone located near the skin is used. Intraosseous infusion also is sometimes used on newborns and small children when suitable blood vessels cannot easily be accessed. Intraosseous infusion requires the penetration by a needle or the like of the patient's skin and outer cortical bone, to gain access to the trabecular bone.

Another need for accessing the trabecular bone arises when a bone marrow sample is to be drawn, or aspirated. Again, a needle or the like must penetrate the patient's skin and outer cortical bone to gain access to the trabecular bone.

Although intraosseous infusion is considered a viable alternative to vascular infusion, it has not met with widespread acceptance. One reason for this is the practical difficulty of penetrating the infusion needle or other device to the proper depth in the bone. Typically, a collar or other stop is fixed on the needle shaft to indicate when the needle has penetrated to a particular depth that is estimated to be within the trabecular bone. This technique is not always effective, however, because it relies on a mere estimate of the required depth and because patients' internal bone structure can vary significantly. These same difficulties apply to the aspirating of bone marrow samples, as well.

Monitoring the resistance to penetration of a conventional infusion or aspiration needle is not always an effective indicator of the needle's position within the bone, either. Generally speaking, the resistance is relatively high when the tip of the needle is moving through the outer cortical bone, and it decreases when the tip reaches the trabecular bone. The resistance increases again if the needle tip reaches the inner cortical bone, on the opposite side of the trabecula. However, such variations in resistance can be very subtle and can vary substantially from one patient to another. Accordingly, monitoring penetration resistance is not considered a completely effective technique for controlling penetration depth.

It should therefore be appreciated that there is a significant need for an intraosseous infusion or aspiration apparatus, and related method, that conveniently and accurately places the tip of an infusion/aspiration needle or tube within a patient's trabecular bone, for an effective infusion of liquid to, or aspiration of bone marrow from, a patient. The present invention fulfills this and other important needs.

SUMMARY OF THE INVENTION

The present invention is embodied in an improved intraosseous infusion and/or aspiration apparatus, and related method, which effectively places the tip of an infusion/aspiration tube within the trabecula of a patient's bone, without a need to estimate the required penetration depth and without the need to precisely monitor the bone's resistance to the penetration. More particularly, the apparatus includes a base having a lower surface adapted for placement against the patient's skin, adjacent the bone into which the liquid is to be infused, or from which marrow is to be aspirated, and an elongated infusion/aspiration tube extending through a bore formed in the base and including a threaded lower end adapted to penetrate the patient's skin and bone. In use, the base is positioned with its lower surface abutting against the patient's skin and the infusion/aspiration tube is then pushed through the skin and rotated about its longitudinal axis, to threadedly advance the tube's lower end through the outer cortical bone and into the trabecular bone. The trabecular bone is known to be reached when continued rotation of the tube no longer advances the tube through the bone. When this position has been reached, the liquid can be infused into the trabecular bone, or the marrow aspirated from it, through a port located in the tube's lower end.

In a separate and independent feature of the invention, the infusion/aspiration tube's lower end is enlarged, to further indicate when the lower end reaches the trabecular bone. In particular, the trabecular bone is known to be reached by the enlarged lower end when a substantial reduction in resistance to continued rotation of the tube is sensed. The enlarged lower end can be used with or without accompanying threads. In the latter case, an axial pressure must be applied to the tube to advance it through the skin and cortical bone.

In one, more detailed feature of the invention, the enlarged lower end of the infusion/aspiration tube is shaped substantially like an American football, with a pointed remote tip. The height of the threads increases smoothly from a minimum at the remote tip to a maximum at the portion of the enlarged lower end having the largest diameter, and the maximum diameter of the threads is preferably about twice the uniform diameter of the tube's unthreaded portion. The fluid preferably exits the tube via two lateral ports located on opposite sides of the enlarged lower end, between adjacent thread crests.

In another feature of the invention, the apparatus further includes a handle attached to the upper end of the infusion/aspiration tube and a compression spring is interposed between the handle and the base, for yieldably urging the handle away from the base. In use, the infusion/aspiration tube is rotated about its longitudinal axis by rotating the handle, and the rotation is terminated when a resistance to the turning diminishes substantially and/or when continued turning no longer continues to advance the tube through the bone. Releasing the handle at this time allows the spring to continuously bias the tube outwardly such that the enlarged lower end abuts against the inner surface of the cortical bone, to seal the hole formed in the cortical bone by the infusion/aspiration tube. The compression spring can take the form of a coil spring located within an upwardly-facing annular recess formed in the body, coaxial with the bore through which the infusion/aspiration tube extends.

Other features and advantages of the present invention should become apparent from the following description of the preferred embodiments, taken in conjunction with the accompanying drawings, which illustrate, by way of example, the principles of the invention.

DESCRIPTION OF THE PREFERRED EMBODIMENTS

Figure 1:
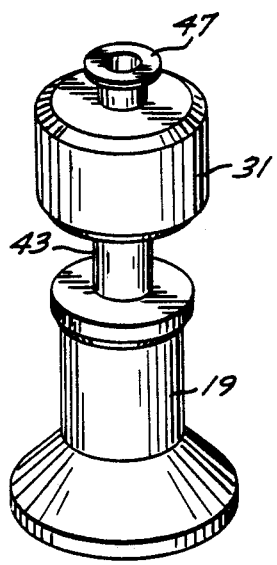
FIG. 1 is a perspective view of a first embodiment of an intraosseous infusion apparatus in accordance with the invention.
Figure 2:
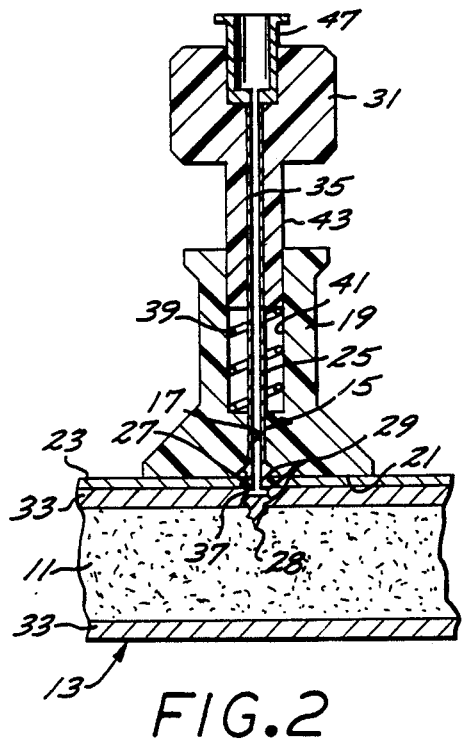
FIG. 2 is a side sectional view of the infusion apparatus of FIG. 1, showing its infusion tube first engaging a patient's skin and cortical bone.
Figure 3:
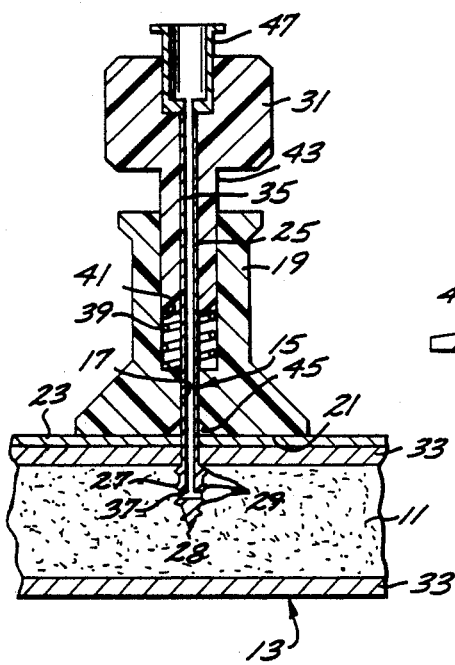
FIG. 3 is a side sectional view similar to FIG. 2, but showing the infusion tube advanced to a point where its enlarged lower end is located; fully within the trabecular bone, with a compression spring biasing the enlarged lower end into abutment with the interior surface of the cortical bone.

With reference now to the drawings, and particularly to FIGS. 1-3, there is shown a first embodiment of an intraosseous infusion apparatus for infusing a liquid (e.g., whole blood, lactated Ringers, hypertonic saline dextran, or a drug solution) into the trabecula 11 of a patient's bone 13. The apparatus is particularly useful in rapidly and reliably providing vascular access for infusion of the liquids into patients for whom there is a difficulty in utilizing the more common vascular infusion, due for example to low blood pressure brought on by severe circulatory shock or hemorrhaging or by small vessel size. Suitable bones include for example the manubrium (sternum), distal femur, proximal tibia, and iliac crest, which are all relatively large and located very close to the skin. Although these particular bones are preferred, any red marrow site can be used.

The apparatus includes an elongated, straight infusion tube 15 mounted for rotation and axial movement within a bore 17 formed in a base 19. The base includes a generally flat lower surface 21 adapted for placement against the patient's skin 23, adjacent the bone 13 into which the liquid is to be infused. The infusion tube includes a shaft section 25 of uniform diameter and a lower end 27 that projects downwardly from the base and includes a sharp, remote tip 28 and external threads 29. A handle 31 connected to an upper end of the tube's shaft section can be manually pushed downwardly to force the sharp tip of the tube into the patient's skin. FIG. 2 shows the apparatus in a position where the sharp tip of the infusion tube's lower end has just reached and entered into the cortex 33 of the bone 13. Thereafter, the handle can be rotated about the infusion tube's longitudinal axis, to thread the tube's lower end through the cortical bone 33 and ultimately into the trabecular bone 11. The liquid can thereafter be infused into the trabecula via the tube's hollow interior 35 and lateral exit ports 37.

In the past, it was difficult to determine precisely when the infusion device, e.g., a needle or threaded tube, had reached the trabecular bone 11. Frequently, in the case of an infusion needle, the needle tip would be stranded in non-bone tissue either short of or beyond the bone. The latter situation of projecting the needle beyond the bone could be particularly dangerous. On the other hand, if the tip of the needle or other device was in the bone, but not the trabecular bone (e.g., the outer or inner cortical bone 33), infusion was difficult, if not impossible, because of the cortical bone's density. No convenient, reliable technique was known for ensuring that the tip of the device was properly positioned within the trabecula.

In accordance with the invention, a proper positioning of the lateral exit ports 37 at the lower end 27 of the infusion tube 15 is ensured by configuring the lower end to be enlarged or bulbous relative to the infusion tube's shaft 25. As the infusion tube is threaded through the cortical bone, its enlarged lower end resiliently deforms the cortical bone radially outwardly. Eventually, the enlarged lower end reaches the trabecula and the cross-sectional size of its portion still within the cortical bone begins to diminish. The cortical bone therefore flexes back radially inwardly and reduces its frictional grip on the advancing tube. When the enlarged lower end fully reaches the trabecula, continued rotation of the tube causes it merely to rotate in place, with no further axial advancement. The trabecula has insufficient structural integrity to be threaded, in most instances. In addition, the trabecula and cortex of the bone together then offer substantially reduced resistance to further rotation of the tube. This is easily sensed by the person operating the apparatus.

In another feature of the invention, a compressed coil spring 39 is interposed between the base 19 and the handle 31, to yieldably urge the handle away from the base. In use, after the enlarged lower end 27 has reached the trabecular bone 11, the handle is released, which allows the spring to bias the handle and infusion tube 15 upwardly. This brings the enlarged lower end into contact with the inwardly-facing surface of the cortical bone 33, to effectively seal the hole just formed in the cortical bone by the advancing tube. This also functions to press the base against the patient's skin 23, sandwiching the patient's skin and cortical bone between the base and the tube's enlarged lower end, to secure the apparatus in place. This position is depicted in FIG. 3. At this time, the liquid can be infused into the trabecula.

To strengthen the infusion tube 15 during its threaded insertion into the patient's bone 13, an elongated stiffener (not shown in the drawings) such as a Trocar rod or stylet can be temporarily placed into the tube's hollow interior 35. After the threaded insertion has been completed, the stiffener is removed, to allow the liquid infusion to take place.

In the embodiment of FIGS. 1–3, the compression spring 39 is located within an annular recess 41 formed in the upper side of the base 19. The recess is axially aligned with the bore 17, such that the spring encircles the infusion tube 15. The handle 31 includes a downward projection 43, concentric with the tube, that is sized to slidably fit within the recess 41. The projection and recess cooperate to maintain the handle and base aligned with each other. Although the spring is depicted as being a compressed coil spring, it will be appreciated that other resilient elements (e.g., a foam rubber block) could alternatively be used.

It will be appreciated that the base 19 can have any of a number of shapes and sizes. Requirements for the base are that it: (1) provide lateral support and alignment for the infusion tube shaft 25 and stabilize the apparatus on the patient's skin 23 when installed, (2) serve as a support for the spring 39, and (3) provide a grip surface for the operator turning the handle 31 relative to it. Similarly, the handle can have any of a number of shapes and sizes, the only significant requirement being that the operator be able to conveniently grasp it. A suitable surface texture (not shown) or other irregularity in the handle's outer surface will facilitate such grasping.

The base 19 and handle 31 may be made from any suitable material having the requisite strength to withstand normal handling. The base may have at least limited pliability and may have a slightly concave lower surface 21, so as to securely engage the patient's skin 23.

Figure 6:
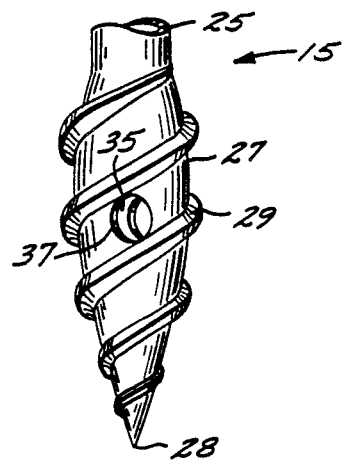
FIG. 6 is an enlarged side view of the enlarged lower end of the infusion tube used in the three embodiments of FIGS. 1-5.

FIG. 6 is an enlarged side view of the infusion tube's enlarged lower end 27. The end has a shape much like an American football, with a continuously-varying diameter that increases smoothly from substantially zero at the sharp, remote tip 28 to a maximum at a midportion of the lower end and then decreases smoothly to a point where the lower end terminates and the tube's uniform diameter shaft section 25 begins. Similarly, the height of the threads increases smoothly from a value of substantially zero at the remote tip 28 to a maximum at the point where the lower end 27 has its maximum diameter and decreases smoothly to substantially zero at the point where the uniform-diameter shaft 25 begins. The threads preferably have a maximum height of about one-third the maximum radius of the enlarged lower end. In addition, the enlarged lower end's maximum thread diameter is preferably about twice the diameter of the uniform-diameter shaft.

The two lateral ports 37 are located on opposite sides of infusion tube's enlarged lower end 27, at the midportion of the lower end having the largest diameter. The two ports are each positioned between two adjacent thread crests.

As shown in FIGS. 2 and 3, the generally flat lower surface 21 of the base 19 functions to stabilize the apparatus on the patient's skin 23. The lower surface can include a countersink 45 encircling the bore 17. This countersink allows the enlarged lower section 27 of the infusion tube 15 to be retracted partially into the base when the apparatus is being stored or is being initially used on a patient.

After the infusion tube 15 has been properly inserted into the patient's bone 13, a liquid can be infused into the bone through the tube and the lateral ports 37 in the tube's enlarged lower end 27. The liquid is delivered to the tube via a standard fluid fitting 47 located at the top side of the handle 31. The fitting is adapted for connection to any conventional infusion device (not shown in the drawings), such as an autoinjection cannister, gravity feed bag, or syringe. The process of inserting the infusion tube into the bone will ordinarily break some of the trabecular bone structure 11, so as to reduce resistance to the infusion. As previously mentioned, the liquid being delivered can be a resuscitation fluid or any other standard vascular delivery drug.

Figure 4:
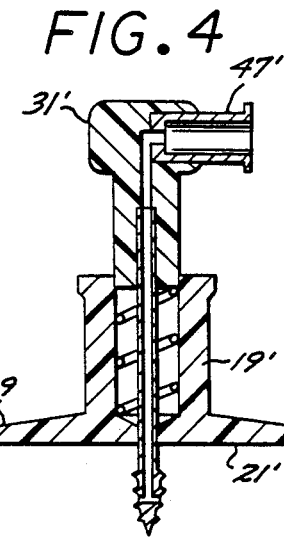
FIG. 4 is a side sectional view of a second embodiment of an intraosseous infusion apparatus in accordance with the invention.

FIG. 4 depicts a second embodiment of an intraosseous infusion apparatus in accordance with the invention. This embodiment is similar to that of FIGS. 1–3, except that the fluid fitting 47' is attached to a side, rather than the top, of the handle 31'. In addition, the base 19' has a lower profile, with an enlarged annular flange 49 that defines the lower surface 21' placed on the patient's skin.

Figure 5:
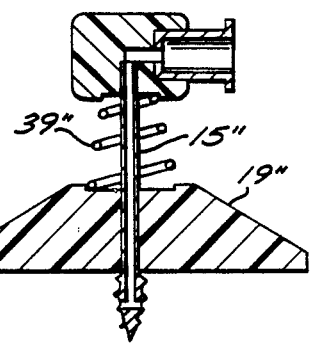
FIG. 5 is a side sectional view of a third embodiment of an intraosseous infusion apparatus in accordance with the invention.

FIG. 5 depicts a third embodiment of an intraosseous infusion apparatus in accordance with the invention. This embodiment is similar to the first two embodiments, except that the base 19" is generally frustoconical and does not include an annular recess for confining the coil spring 39". Instead, the coil spring has a generally frusto-conical shape so that when it is fully compressed, its successive turns nest tightly together and provide a reduced height. The base, itself, guides the infusion tube 15" vertically into the patient's bone.

Figure 7:
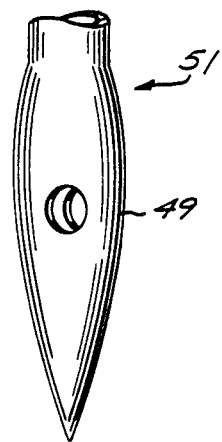
FIG. 7 is an enlarged side view of the lower end of an alternative, unthreaded infusion tube suitable for use in the three embodiments of FIGS. 1-5.

FIG. 7 depicts the enlarged lower end 49 of an infusion tube 51 that can be used in place of the infusion tube 15 of the intraosseous infusion apparatus embodiments of FIGS. 1–5. The enlarged lower end of this alternative tube 51 has the same general shape as the enlarged lower end 27 of the tube 15 (FIG. 6), described above, but it is unthreaded. Axial advancement of this alternative tube through the patient's bone 13 requires an axial force to be applied using the handle. In use, the reaching of the trabecular bone 11 is sensed only by a substantial reduction in resistance to continued advancement of the tube.

Figure 8:
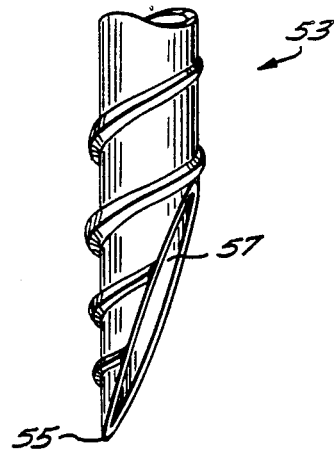
FIG. 8 is an enlarged side view of the lower end of an alternative, uniform-diameter infusion tube suitable for use in the three embodiments of FIGS. 1-5.

FIG. 8 depicts the lower end of yet another infusion tube 53 that can be used in place of the infusion tube 15 of the intraosseous infusion apparatus embodiments of FIGS. 1–5. The lower end of this tube 53 is threaded, but not enlarged, and it is beveled to produce a sharp tip 55 for penetrating the patient's skin 23 and bone 13 and to produce a large port 57 delivering the infusion liquid. In use, the reaching of the trabecular bone 11 is sensed only by a failure of the tube to continue its axial advancement as it is being rotated about its longitudinal axis. As described above, a Trocar rod or stylet (not shown) can be temporarily placed into the tube's hollow interior, both to stiffen the tube and to prevent skin tissue from plugging the tube.

One important safety feature of the embodiments of the invention that use an infusion tube with a threaded lower end (FIGS. 6 and 8) is that the tip of the tube cannot inadvertently penetrate excessively beyond the inner cortical bone 33. In some unusual circumstances, the infusion tube can inadvertently be threaded through the trabecular bone 11 and into the inner cortical bone. However, after continued rotation advances the tube's threaded lower end fully through the inner cortical bone, it cannot advance further. Continued rotation of the tube simply causes it to rotate in place. This protects vital body parts (e.g., the heart, lungs and great vessels, in the case of the sternum) from injury.

It will be appreciated that the various embodiments above alternatively can be used to aspirate marrow from the patient's bone 13, rather than infuse a liquid into it. No significant alterations need be made to the embodiments, other than to adapt the upper end of the tube 15 (now an aspiration tube) for connection to a suitable aspirator.

It should be appreciated from the foregoing description that the present invention provides an improved apparatus and related method for infusing liquids into, and/or aspirating marrow from the trabecula of a patient's bone. The apparatus enables the user to reliably determine when an enlarged, threaded tip of an infusion/aspiration tube has reached the trabecular bone, and a spring bias ensures that the tip seals the hole formed in cortical bone during the subsequent infusion or aspiration.

Although the invention has been described in detail with reference to the presently preferred embodiments, those of ordinary skill in the art will appreciate that various modifications can be made without departing from the invention. Accordingly, the invention is defined only by the following claims.

We claim:

1. Apparatus for infusing a liquid into, or aspirating marrow from, the trabecula of a patient's bone, comprising:
    a base having a lower surface adapted for placement against the skin of a patient, adjacent to a bone of the patient, wherein a bore extends through the base, emerging in its lower surface; and
    an elongated infusion/aspiration tube extending through the bore formed in the base, wherein the tube includes an upper end and an enlarged lower end adapted to penetrate the patient's skin and bone, the enlarged lower end including a port communicating with the tube's hollow interior;
    wherein, in use, the base is positioned with its lower surface abutting against the patient's skin, adjacent the bone, and the infusion/aspiration tube is then rotated about its longitudinal axis, to advance the tube's enlarged lower end through the cortical bone and into the trabecular bone, the reaching of the trabecular bone being sensed by a substantial reduction in resistance to continued rotation of the tube;
    and wherein the liquid can thereafter be infused into, or marrow aspirated from, the trabecular bone through the tube and its port.

2. Apparatus as defined in claim 1, wherein the infusion/aspiration tube's enlarged lower end further includes threads for engaging and threadedly advancing the tube's lower end through the patient's cortical bone.

3. Apparatus as defined in claim 2, wherein the infusion/aspiration tube's enlarged lower end includes two lateral ports located on its opposite sides, between adjacent thread crests, both lateral ports communicating with the tube's hollow interior.

4. Apparatus as defined in claim 2, wherein:
    the infusion/aspiration tube has a predetermined uniform diameter along a substantial portion of its length, terminating at the tube's enlarged lower end; and
    the infusion/aspiration tube's enlarged lower end is shaped substantially like an American football, with a pointed remote tip.

5. Apparatus as defined in claim 4, wherein the height of the threads on the enlarged lower end of the infusion/aspiration tube increases smoothly from a minimum at the remote tip to a maximum at the portion of the enlarged lower end having the largest diameter.

6. Apparatus as defined in claim 5, wherein the maximum diameter of the threads is about twice the predetermined uniform diameter of the infusion/aspiration tube.

7. Apparatus as defined in claim 1, wherein:
    the apparatus further includes
        a handle attached to the upper end of the infusion/aspiration tube, and
        a compression spring interposed between the handle and the base, for yieldably urging the handle away from the base;
    the infusion/aspiration tube is rotatable about its longitudinal axis by rotating the handle; and
    terminating the rotating of the handle after the infusion/aspiration tube's enlarged lower end has reached the trabecular bone allows the spring to urge the tube upwardly such that the tube's enlarged lower end abuts against the inner surface of the cortical bone, to seal the hole formed in the cortical bone by the tube's enlarged lower end.

8. Apparatus as defined i claim 7, wherein:
    the body includes an annular recess aligned with the bore, which extends the infusion/aspiration tube; and
    the compression spring is a coil spring located within the body's annular recess, encircling the infusion/aspiration tube.

9. Apparatus as defined in claim 1, wherein:
    the base's lower surface is generally flat; and
    the bore extends through a mid-portion of the base's lower surface, substantially perpendicular to the surface.

10. A method for infusing a liquid into, or aspirating marrow from, the trabecula of a patient's bone using an infusion/aspiration apparatus that includes a base adapted for placement against the patient's skin, adjacent the bone into which the liquid is to be infused, or from Which marrow is to be aspirated, and an elongated infusion/aspiration tube extending through a bore in the base and having an enlarged lower e-d with a sharp tip and with a port communicating with the tube's hollow interior, the method comprising steps of:
    rotating the infusion/aspiration tube about its longitudinal axis such that the tube's enlarged lower end engages and advances through the patient's skin and cortical bone and into the trabecular bone;
    terminating the step or rotating when a substantial reduction in resistance to rotation is sensed, indicating that the infusion/aspiration tube's enlarged lower end has reached the trabecular bone; and
    injecting the liquid into, or aspirating marrow from, the trabecular bone through the infusion/aspiration tube and the port in the tube's enlarged lower end.

11. A method as defined in claim 10, wherein:
    the infusion/aspiration apparatus further includes
        a handle connected to an end of the infusion/aspiration tube opposite its enlarged lower end, and
        a compression spring interposed between the handle and the base for urging the handle away from the base;

the step of rotating includes a step of rotating the handle; and the step of terminating includes a step of releasing the handle, such that the compression spring urges the handle and infusion/aspiration tube upwardly, to bring the tube's enlarged lower end into abutment with the inner surface of the cortical bone and seal the hole formed in the cortical bone by the tube's enlarged lower end.

12. A method as defined in claim 10, wherein:

the infusion/aspiration tube's enlarged lower end includes threads for engaging and threadedly advancing the tube's lower end through the cortical bone; and the step of rotating the infusion/aspiration tube advances the tube's enlarged lower end through the cortical bone without the need for an axial force along the tube.

13. Apparatus for infusing a liquid into, or aspirating marrow from, the trabecula of a patient's bone, comprising:

a base having a generally flat lower surface adapted for placement against the skin of a patient, adjacent to a bone into the trabecula of which a liquid is to be infused or marrow is to be aspirated, wherein a bore extends through the base, emerging in its lower surface and oriented substantially perpendicular to the lower surface;

an elongated infusion/aspiration tube extending through the bore formed in the base, wherein the tube includes an upper end and an enlarged lower end adapted to penetrate the patient's skin and bone, wherein the enlarged lower end is shaped substantially like an American football, with a pointed remote tip and with external threads, and wherein the enlarged lower end includes two lateral ports located on its opposite sides, between adjacent thread crests, both lateral ports communicating with the tube's hollow interior;

a handle attached to the upper end of the infusion/aspiration tube; and a compression spring interposed between the handle and the base, for yieldably urging the handle away from the base;

wherein, in use, the base is positioned with its flat lower surface abutting against the patient's skin, adjacent the bone into which the liquid is to be infused or from which marrow is to be aspirated, and the infusion tube is then rotated using the handle about the tube's longitudinal axis, to threadedly advance the tube's enlarged lower end through the cortical bone and into the trabecular bone, the reaching of the trabecular bone being sensed and by a terminating of the axial advancement and by a substantial reduction in resistance to continued rotation of the tube;

wherein terminating the rotating of the handle after the infusion/aspiration tube's enlarged lower end has reached the trabecular bone allows the spring to urge the tube upwardly such that the tube's enlarged lower end abuts against the inner surface of the cortical bone, to seal the hole formed in the cortical bone by the tube's enlarged lower end;

and wherein the liquid can thereafter be infused into, or marrow aspirated from, the trabecular bone through the tube and its ports.

14. Apparatus as defined in claim 13, wherein:

the infusion/aspiration tube has a predetermined uniform diameter along a substantial portion of its length, terminating at the tube's enlarged lower end;

the height of the threads on the enlarged lower end of the infusion/aspiration tube increases smoothly from a minimum at the remote tip to a maximum at the portion of the enlarged lower end having the largest diameter; and the maximum diameter of the threads is about twice the predetermined uniform diameter of the infusion/aspiration tube.

15. Apparatus for infusing a liquid into, or aspirating marrow from, the trabecula of a patient's bone, comprising:

a base having a lower surface adapted for placement against the skin of a patient, adjacent to a bone into the trabecula of which a liquid is to be infused or from which marrow is to be aspirated, wherein a bore extends through the base, emerging in its lower surface; and an elongated infusion/aspiration tube extending through the bore formed in the base, wherein the tube includes an upper end and a lower end adapted to penetrate the patient's skin and bone, the lower end including threads and a port fixed relative to the threads and communicating with the tube's hollow interior;

wherein, in use, the base is positioned with its lower surface abutting against the patient's skin, adjacent the bone, and the infusion/aspiration tube is then rotated about its longitudinal axis, to threadedly advance the tube's lower end through the cortical bone and into the relatively porous trabecular bone, whereupon continued rotation of the tube no longer threadedly advances the tube through the bone;

and wherein the liquid can thereafter be infused into, or marrow aspirated from, the trabecular bone through the tube and its port.

16. Apparatus as defined in claim 15, wherein:

the lower end of the infusion/aspiration tube, at the site of the threads, is enlarged and shaped substantially like an American football, with a pointed remote tip, such that a substantial reduction in resistance to rotation occurs when the tube's lower end threadedly advances to the trabecular bone; and the remaining portion of the infusion/aspiration tube has a substantially uniform diameter.

17. Apparatus as defined in claim 15, wherein the port included at the lower end of the infusion/aspiration tube is located between adjacent crests of the threads.

18. A method for infusing a liquid into, or aspirating marrow from, the trabecula of a patient's bone using an infusion/aspiration apparatus that includes a base adapted for placement against the patient's skin, adjacent the bone into which the liquid is to be infused or from which marrow is to be aspirated, and an elongated infusion/aspiration tube extending through a bore in the base and having a threaded lower end with a sharp tip and with a port fixed relative to the threads and communicating with the tube's hollow interior, the method comprising steps of:

rotating the infusion/aspiration tube about its longitudinal axis such that the tube's lower end threadedly engages and advances through the patient's skin and cortical bone and into the trabecular bone;

terminating the step of rotating when rotation no longer threadedly advances the tube through the bone, indicating that the infusion/aspiration tube's lower end has reached the trabecular bone; and infusing the liquid into, or aspirating marrow from, the trabecular bone through the infusion/aspiration tube and the port in the tube's threaded lower end.

19. A method as defined in claim 18, wherein:

the lower end of the infusion/aspiration tube, at the site of the threads, is enlarged and shaped substantially like an American football, with a pointed remote tip; and the method further includes a step of terminating the step of rotating when a substantial reduction in resistance to rotation is sensed, indicating that the infusion/aspiration tube's enlarged lower end has reached the trabecular bone.

20. A method as defined in claim 19, wherein:

the infusion/aspiration apparatus further includes
    a handle connected to an end of the infusion/aspiration tube opposite its enlarged lower end, and
    a compression spring interposed between the handle and the base, for urging the handle away from the base;

the step of rotating includes a step of rotating the handle; and the step of terminating includes a step of releasing the handle, such that the compression spring urges the handle and the infusion/aspiration tube upwardly, to bring the tube's enlarged lower end into abutment with the inner surface of the cortical bone and thereby seal the hole formed in the cortical bone by the tube's enlarged lower end.

* * * * *

UNITED STATES PATENT AND TRADEMARK OFFICE
CERTIFICATE OF CORRECTION

PATENT NO. : 4,969,870

DATED : November 13, 1990

INVENTOR(S) : George C. Kramer et al.

It is certified that error appears in the above-identified patent and that said Letters Patent is hereby corrected as shown below:

In column 1, before "Background of the Invention," insert the following paragraph:

-- This invention was made with Government support under Contract No. DAMD17-88C-8127 awarded by the U.S. Army Medical Research Acquisition Activity (USAMRAA). The Government has certain rights in this invention. --

Signed and Sealed this

Thirteenth Day of April, 1993

Attest:

STEPHEN G. KUNIN

*Attesting Officer*  *Acting Commissioner of Patents and Trademarks*